United States Patent [19]

Van Niekerk

[11] Patent Number: 5,179,859
[45] Date of Patent: Jan. 19, 1993

[54] METHOD OF SAMPLING, AND SAMPLING DEVICE

[75] Inventor: Johannes A. Van Niekerk, Caledon, South Africa

[73] Assignee: Caledon Riviersonderend Kooperasie Beperk, South Africa

[21] Appl. No.: 661,557

[22] Filed: Feb. 26, 1991

[30] Foreign Application Priority Data

Mar. 16, 1989 [ZA] South Africa ............. 90/2058

[51] Int. Cl.⁵ .............................. G01N 1/12
[52] U.S. Cl. ................................. 73/864.64
[58] Field of Search .......... 73/864.51, 863.31, 864.63, 73/864.64

[56] References Cited

U.S. PATENT DOCUMENTS

| | | | |
|---|---|---|---|
| 230,121 | 7/1880 | Frost | 73/863.31 |
| 1,168,486 | 1/1916 | Des Isles | 73/864.51 X |
| 2,688,877 | 9/1954 | Peine | 73/864.64 |
| 3,091,968 | 6/1963 | Platzer | 73/863.31 |

OTHER PUBLICATIONS

Degesh America, Inc., Smart Probe, single page pamphlet.

*Primary Examiner*—Jerry W. Myracle
*Attorney, Agent, or Firm*—Ladas & Parry

[57] ABSTRACT

In sampling grain offered in bulk as shown at 40, a sampling device 10 is inserted vertically downwardly into the grain. The device 10 has an inner tube 12 having openings 18 in series along its length and a sleeve 14 which is open bottomed and axially slidable over the tube. During insertion, the sleeve 14 covers the openings 18. To obtain a sample, the sleeve 14 is slowly slid upwardly relative to the inner tube thus progressively to expose the openings 18 from the bottom upwardly. Grain flows laterally via the openings 18 into the tube, which fills from the bottom. Practically no vertical displacement of kernels takes place, thus ensuring that a representative sample is taken at all levels. Ultimately, the sleeve 14 is slid downwardly to close the openings 18. The device, containing the sample, is withdrawn.

13 Claims, 4 Drawing Sheets

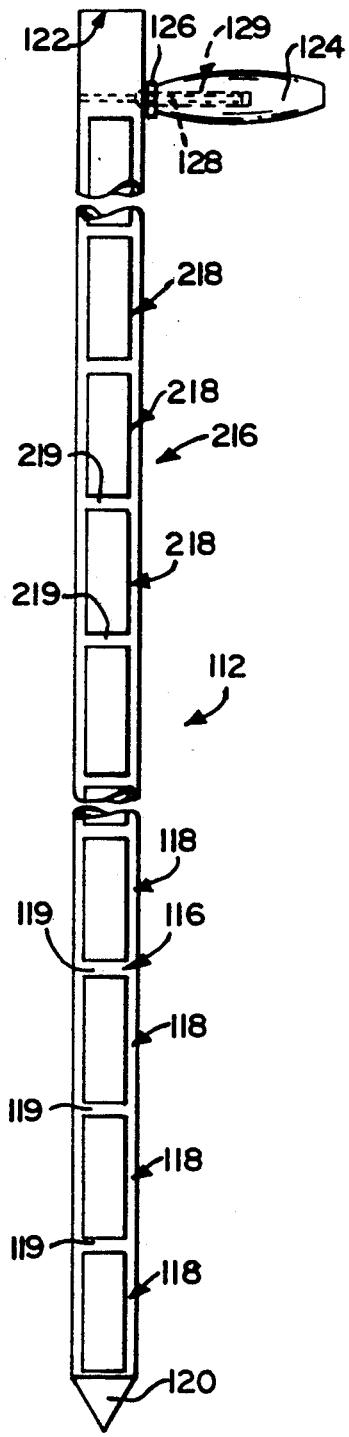
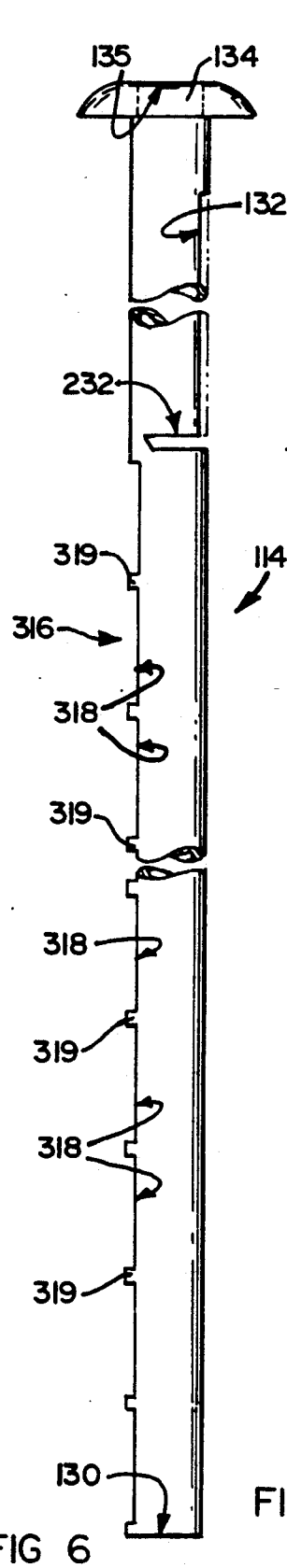
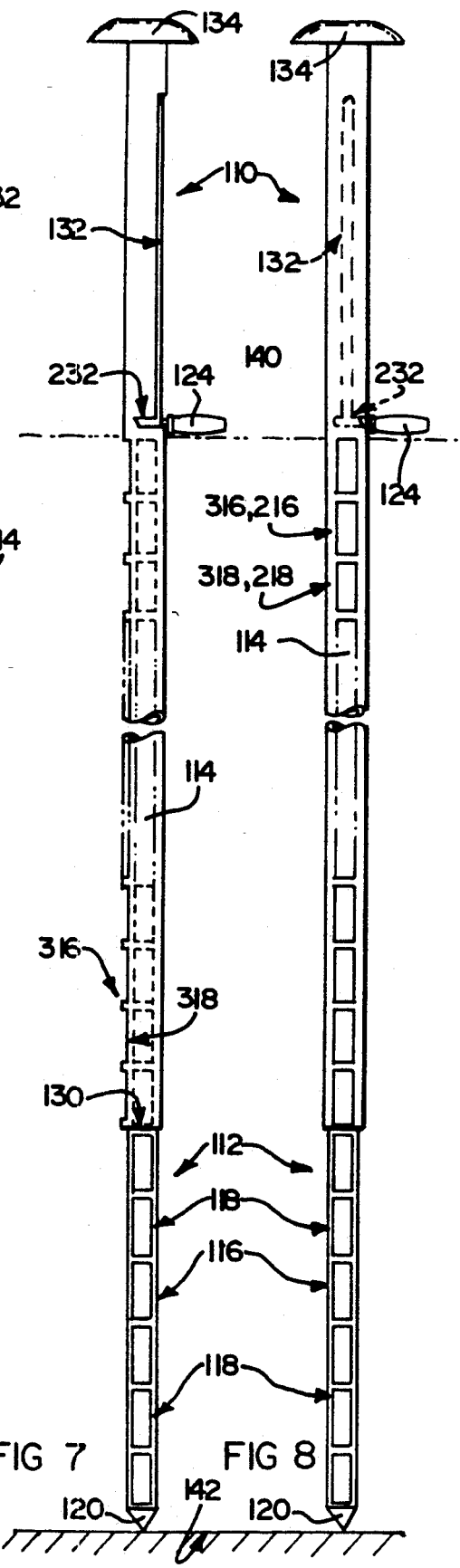
FIG 5   FIG 6   FIG 7   FIG 8

METHOD OF SAMPLING, AND SAMPLING DEVICE

This invention relates to a method of sampling and to a sampling device. It relates more specifically to sampling of grain offered in bulk such as wheat, barley, maize, sorghum, beans, sunflower and the like.

It has become common practice in modern farming for producers to deliver grain to depots in mass reservoirs (e.g. lorries, trailers, railway trucks, and the like) which reservoirs have peripherally closed load areas. It is very important readily and quickly to obtain representative samples from such loads to measure the quality, moisture content, purity and the like of the grain.

It is an object of this invention to provide a method of and a device for sampling such grain which are better able to obtain a representative sample than other methods and devices known to the Inventor.

In accordance with the invention, there is provided a method of sampling grain offered in bulk, including inserting an empty, elongate container substantially vertically into the bulk of grain while covering elongate inlet means of the container;

uncovering the inlet means and exposing the interior of the container progressively from the bottom of the bulk upwardly to allow grain, correspondingly progressively, to flow into the container from a position toward the bottom of the bulk to a position upwardly spaced from the bottom of the bulk; and withdrawing the container to collect a sample.

It is vital to appreciate the importance of exposing the interior of the container to the grain progressively from the bottom to the top. The Applicant does not wish to be bound by theory, but an explanation of the Inventor's understanding of the mechanisms involved in flow of grain into the container may promote a proper understanding of the invention.

Because grain is of a particulate nature, although it is able to flow, its conduct during flow or mechanism of flow is different to that of a liquid in many respects. This difference is due inter-alia, possibly mainly, to the effect of friction among touching kernels. Friction, and forces created by friction, increase with depth because of the increasing weight bearing on a particular kernel. These frictional forces inhibit displacement of the kernels.

The Inventor has appreciated, first, that the deeper in a bulk of grain a kernel finds itself, the less it is able to move under the influence of gravity or other external forces. Second, the Inventor has found, when grain flows into a container through an opening spaced well below the level of the grain, that the grain does not rise in the container above the level of the opening, or if it does rise, it rises only to a very limited degree. Thus, grain does not "flow upwardly" in a container under the influence of the "head" of grain in the bulk surrounding the container. Third, the Inventor has appreciated that grain does fall down in a container under gravity.

Thus, when, in accordance with the invention, the interior of the container inserted into a bulk of grain is exposed to the grain progressively from bottom to top, the slow moving kernels at the bottom can flow laterally into the container without competing with kernels falling from above. As mentioned above, the level of the sample in the container does not rise above the level of the opening, thus kernels will not flow upwardly in the container. In this fashion, it is ensured that a sample kernel at any particular level in the container originates from the bulk of grain at that level.

Inserting of the container is preferably down to the bottom of the bulk.

The method may advantageously include agitating the grain where the inlet means is being exposed.

By way of development, when sampling takes place from a grain reservoir of a depth more than about 1,5 m, uncovering the inlet means and exposing the interior of the container may take place in respect of a lower portion of the bulk of grain, and the method may further include, in respect of a higher portion of the bulk of grain and subsequent to the step in respect of the lower portion of the bulk of grain, exposing the interior of the container to said higher portion substantially simultaneously and allowing the grain from said higher portion to flow into the container.

Then, exposing the interior of the container to said higher portion may include bringing an opening in the container and an opening in a sleeve surrounding the container at a depth corresponding to the position of said higher portion, into register.

It is to be appreciated that the sample of the higher portion of the bulk of grain is taken only when the container has been filled with sample grain up to the level of the lower portion of grain. Thus, kernels from the higher portion cannot fall into the container to a position lower than the boundary of the lower portion of the bulk of grain. Thus, the advantages mentioned in respect of the first aspect, are obtained at least in respect of the lower portion of grain in a deep container.

The invention extends to a sampling device suitable for use in sampling grain offered in bulk, the device comprising a container of elongate shape having a closed lower end adapted for insertion into a bulk of grain;

inlet means extending from about the closed lower end along the container;

closing means for selectively covering the inlet means and operable for progressively exposing the inlet means commencing from said lower end.

The container may conveniently be in the form of a round cylindrical tube.

The inlet means may include a composite opening formed of a plurality of ports arranged in series. The ports may be in longitudinal alignment.

The closing means may include an open ended sleeve fitting snugly, such as to allow axial sliding, over the tube.

The tube may have a laterally extending handle toward an upper end thereof and the sleeve may then have a corresponding slot to allow passage of the handle during axial sliding of the sleeve relative to the container in use. The sleeve may have a handle at or toward an upper end thereof.

By way of development, the sampling device may be adapted to sample grain from a reservoir of a depth more than about 1,5 m. Then, in the device, the inlet means may be in the form of lower inlet means extending from about the closed lower end along a lower portion of the container; and the closing means may be in the form of lower closing means for selectively covering the lower inlet means and operable for progressively exposing the lower inlet means commencing from said lower end. The device may then further include higher inlet means extending from a position beyond the lower inlet means along a higher portion of the container; and higher closing means for selectively covering the higher inlet means and operable for substantially simultaneously exposing the higher inlet means after the lower inlet means has been exposed.

The higher inlet means may substantially be an extension of the lower inlet means. The higher closing means may include exposing means in the form of a series of ports along a predetermined portion of the length of the sleeve, said ports being angularly offset from the higher inlet means, and the sleeve may be adapted to be twisted in use to register the ports with the higher inlet means.

The invention is now described by way of example with reference to the accompanying diagrammatic drawings. In the drawings FIG. 1 shows, in side view, fragmentarily, a sampling device in accordance with a first aspect of the invention;

FIGS. 2 and 3 correspond to FIG. 1 and show respectively an inner tube and an outer sleeve of the sampling device of FIG. 1;

FIGS. 5 and 6 show, respectively in side view, an inner tube and an outer sleeve of a sampling device in accordance with a second aspect of the invention;

FIG. 7 shows the sampling device in accordance with the second aspect of the invention in use in its condition after an initial step of obtaining a sample has been effected;

FIG. 8 shows the sampling device of FIG. 7 but after a further step in obtaining a sample has been effected;

Figure 1:
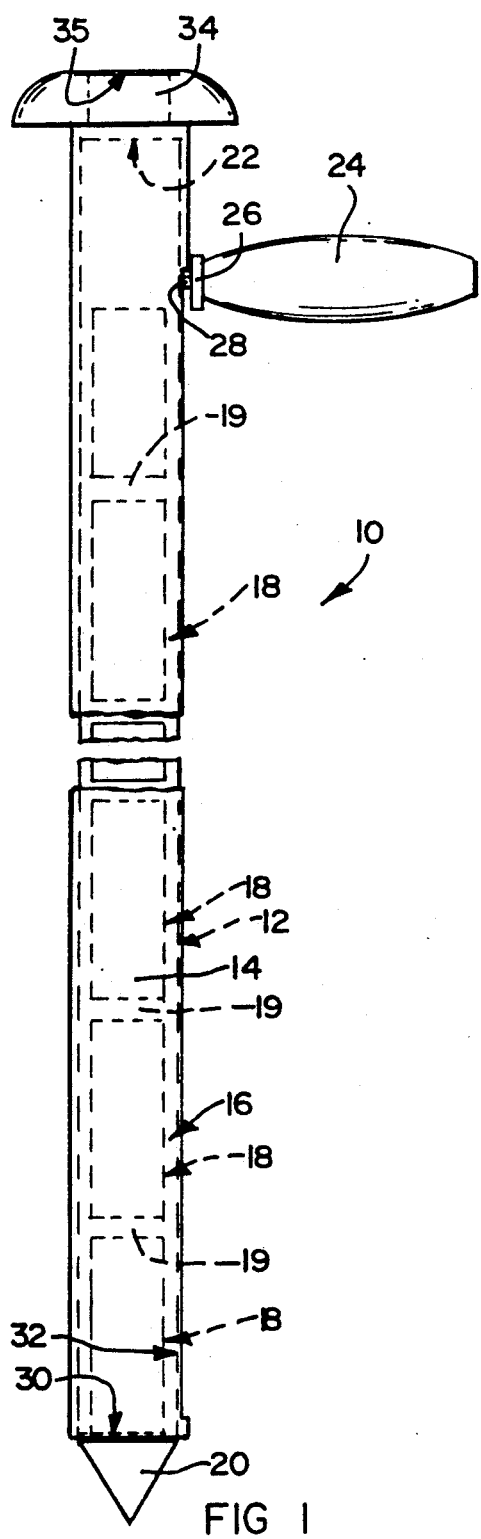
Figure 2:
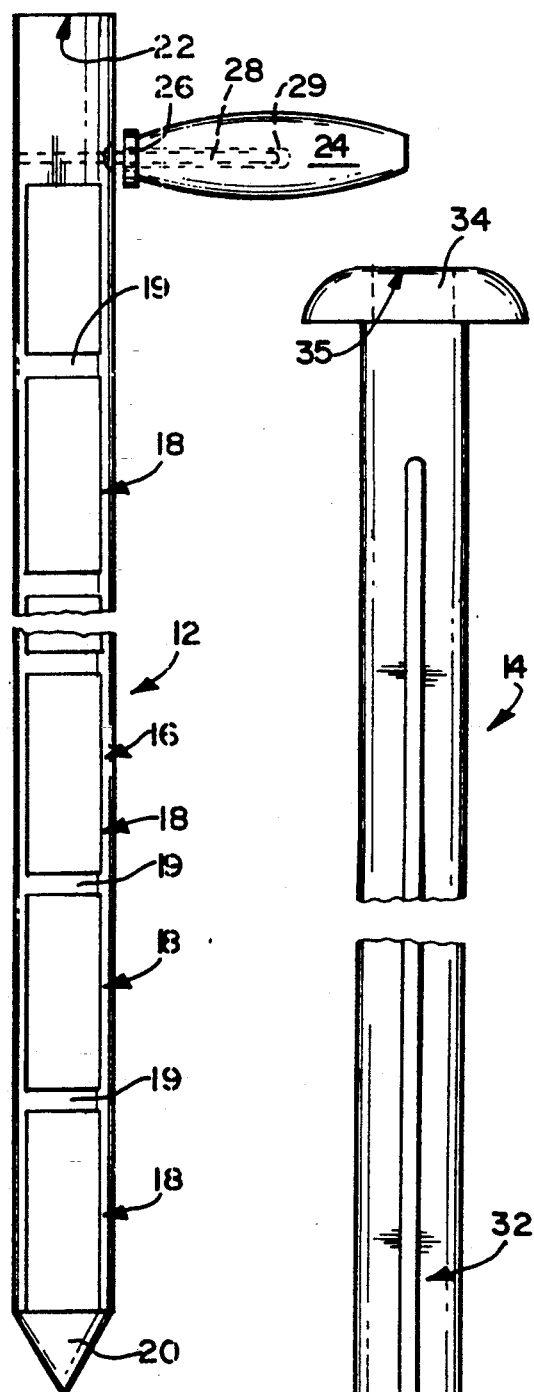
Figure 3:
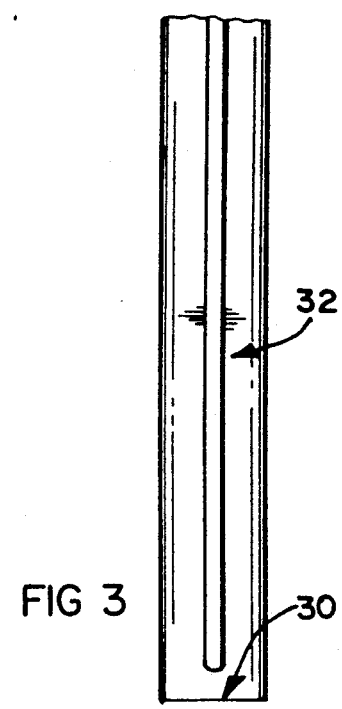

With reference to FIGS. 1, 2 and 3 of the drawings, a sampling device in accordance with a first aspect of the invention is generally indicated by reference numeral 10. It comprises an inner tube 12 and an outer tube 14 fitting snugly, slidably over the inner tube 12.

The inner tube 12 has inlet means generally indicated by reference numeral 16 and comprising a plurality of inlet ports 18 arranged in line along the length of the tube 12. Strengthening ribs 19 divide adjacent ports 18 from each other. At one end, which will be a lower end in use, the tube 12 has a pointed lower end 20. Its opposed, upper end 22, is open.

Toward its open upper end 22, there is provided a transverse handle 24 having a flange 26 and a screw threaded socket 29 co-axial therewith and open at the end of the flange 26. The handle 24 is screwed over a screw threaded shank 28 fixed to the tube 12 toward its upper end and projecting transversely therefrom.

The outer sleeve 14 is open-ended as shown at 30 and 35. Along substantially, but not quite, the whole of its length, it has a longitudinal slot 32 through which the shank 28 is received and which allows passage of the shank 28 when the sleeve 14 is slid along the inner tube 12.

Toward one end, which will be an upper end in use, it has an annular handle 34.

Figure 4:
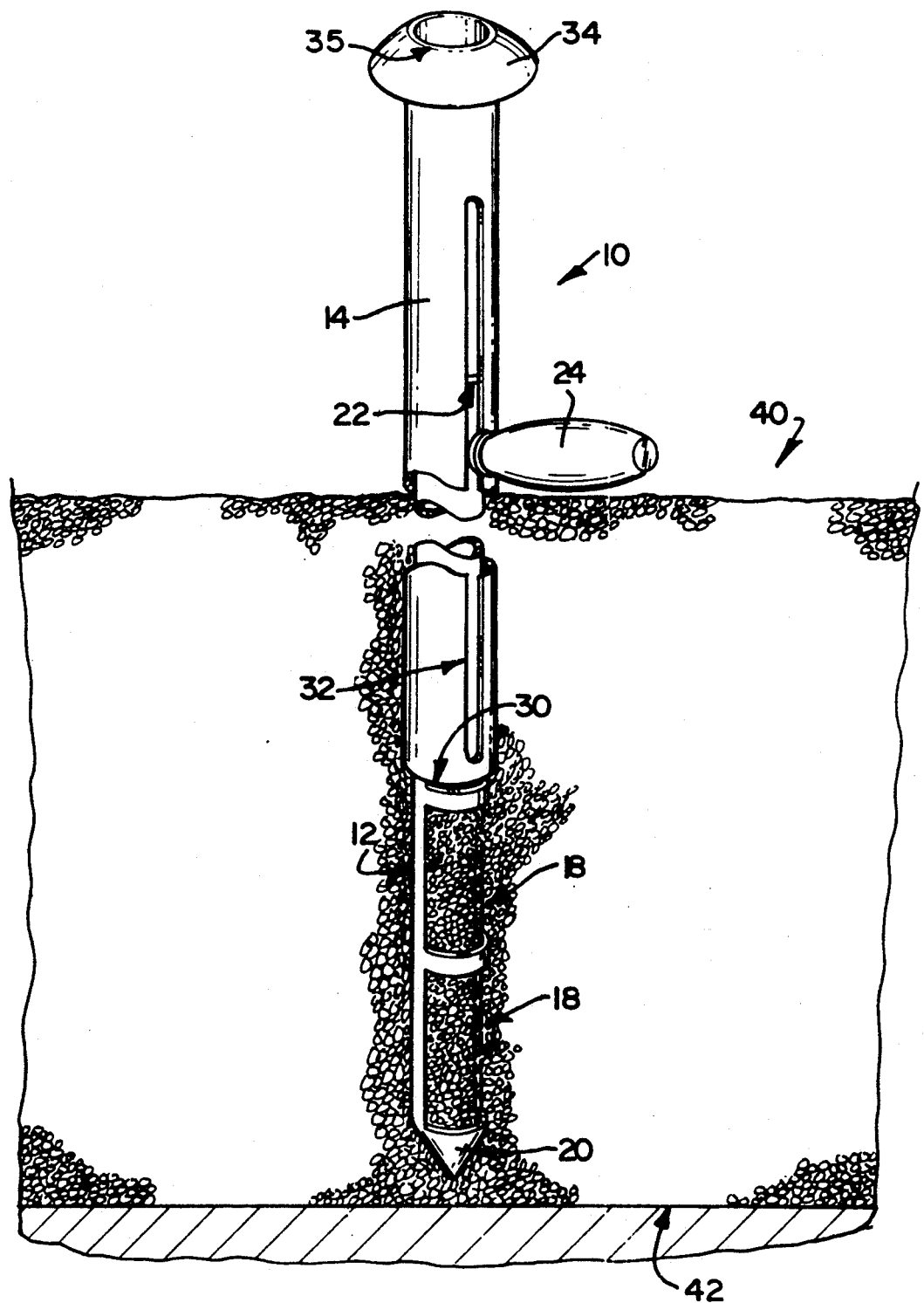
FIG. 4 shows the sampling device of FIG. 1 in use.

With reference also to FIG. 4, the device 10 is shown in use taking a sample from a bulk of grain 40 contained in a reservoir such as the load area of a trailer, represented by its bottom or floor as indicated by reference numeral 42.

With the sleeve 14 fully slid over the tube 12, which is empty, i.e. substantially in the condition shown in FIG. 1, the device 10 is pushed into the grain 40, ideally down to the bottom 42 of the reservoir.

While the inner tube 12 is held in position via the handle 24, the sleeve 14 is slowly extracted by means of its handle 34. Such extraction continues until the shank 28 is stopped against the bottom of the slot 32 or until it has been withdrawn beyond the upper level of the grain 40. The sleeve 14 is then reinserted over the tube 12 and can be locked in position by suitably screwing the handle 24 such that the sleeve 14 is frictionally held between the inner tube 12 and the flange 26 of the handle 24.

The device 10 is then withdrawn from the grain 40 and the sample is emptied into a sample container via the open ends 22, 35 respectively of the inner tube 12 and the sleeve 14.

In operation, when the sleeve 14 commences being withdrawn from the inner tube 12, the interior of the inner tube 12 is progressively, slowly exposed to the grain 40 via the ports 18.

It is to be appreciated that the bottom end 30 of the sleeve 14, which has finite thickness, at least slightly agitates the kernels when it is withdrawn. It is believed that such slight agitation is useful in overcoming static friction amongst kernels and facilitates flowing of kernels through the ports 18 into the tube 12.

As explained above, kernels flow laterally into the interior of the tube 12 and do not rise above the level to which the ports 18 are momentarily opened. In this fashion, kernels are charged as sample kernels into the tube 12 at levels corresponding to the levels of the kernels in the bulk of grain 40. Thus, a representative sample of grain is obtained.

A developed embodiment in accordance with the second aspect of the invention is now described with reference to FIGS. 5, 6, 7, and 8. In many respects, the sampling device 110 in accordance with the second aspect of the invention is similar to the sampling device 10 of FIG. 1. For convenience, similar components or features are indicated by similar reference numerals. Those similar features are not again described, and emphasis is placed on the differences between the sampling devices.

With reference more specifically to FIG. 5, the sampling device 112 is substantially longer than the sampling device 12. It has been found by the Applicant that the first aspect of the invention can conveniently be performed by means of sampling devices up to about 1 m or slightly longer. For reservoirs substantially deeper than 1 m, sampling devices in accordance with the second aspect of the invention and of corresponding length are employed.

Lower inlet means 116, comprising lower ports 118, is provided along a lower portion of the tube 112, typically of a length of about 1 meter.

Beyond the lower portion, which boundary need not be specifically defined on the tube 112, higher inlet means 216 comprising a plurality of aligned ports 218 is provided. The higher inlet means extend up to about the level of the transverse handle 124.

The sleeve 114 in accordance with the second aspect of the invention, is now described with reference more specifically to FIG. 6.

The sleeve 114 is of a length corresponding to that of the tube 112 and has open lower and upper ends 130, 135. It has a slot 132, toward its upper end, and corresponding in length to the length along which the lower inlet means 116 is provided in the tube 112. At a lower extremity of the slot 132, a part circumferential slot 232 is provided. The slot 232 will extend along about 90° of the circumference of the sleeve 114.

The sleeve 114 has, from a position immediately above its lower open end 130, and for a length corresponding to the length of the higher inlet means 216 of the tube 112, exposing means 316 in the form of a plurality of ports 318 corresponding in size and shape, and spacing with the ports 218 of the higher inlet means 216.

With reference to FIGS. 7 and 8, when a sample is to be taken from grain 140 lying at a great depth, say two to three meters, e.g. in a railway truck 142, the device 110 is inserted when in its empty, closed condition into the bulk of grain 140 to the bottom 142 of the reservoir.

Initially, the sleeve 114 is slowly withdrawn through a distance corresponding to the lower portion of grain to be sampled, in accordance with the second aspect of the invention. This operation takes place substantially identically as described with reference to FIG. 4. The condition at the end of this step is indicated in FIG. 7. At that stage, the lower inlet means 116 has been exposed progressively from bottom to top substantially identically to exposure in accordance with the first aspect of the invention to provide a representative sample of grain in the lower portion of the tube 112.

Subsequently, while the handle 124 is held by one hand, the annular handle 135 and thus also the sleeve 114 is twisted through about 90°. This twisting action is allowed by the part circumferential slot 232 allowing passage of the shank of the handle 124 through the twisting angle.

Such twisting registers the exposure ports 318 with the higher inlet ports 218 and thus allows grain to pour substantially simultaneously into the tube 112. It is to be appreciated that the tube 112 will already have been filled to the level of the lower portion. Thus, the higher portion of grain will be sampled in the higher portion of the tube 112.

The Inventor appreciates that sampling of the higher portion is not a representative sample to the same high degree as the sample of the lower portion. Nevertheless, the Inventor knows by experience that so-called "bad" grain is normally hidden in the lower portion of a reservoir and the Inventor believes that such "bad" grain will be sampled via the lower inlet means.

Figure 9:
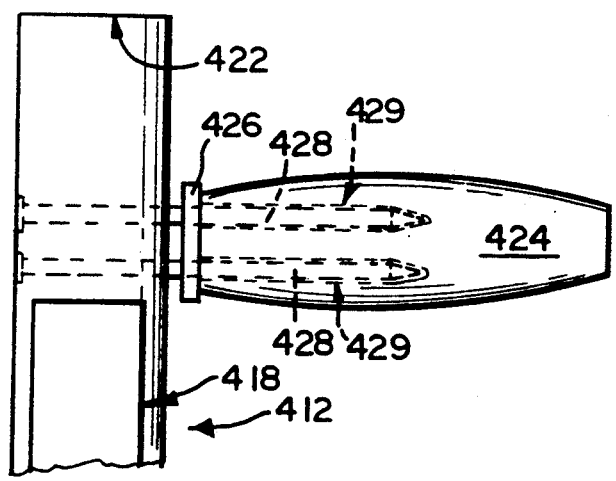
FIG. 9 shows in a view corresponding to FIG. 2, a developed configuration for a handle of the inner tube.

With reference to FIG. 9, advantageously, the handle indicated at 424 is mounted by means of a pair of fixed screws or bolts 428 which are aligned on the axis of the tube 412. The handle 424 thus is not capable of being twisted to nip the sleeve as in the FIG. 2 embodiment, but it is more securely mounted.

Advantageously, the material of the outer tube may be harder than that of the inner tube. For example, the outer tube may be of 304 grade stainless steel and the inner tube of 316 grade stainless steel. It has been found that the strengthening ribs 19, 119, 219, 319 should be at least about 20 mm wide for typical application.

Figure 10:
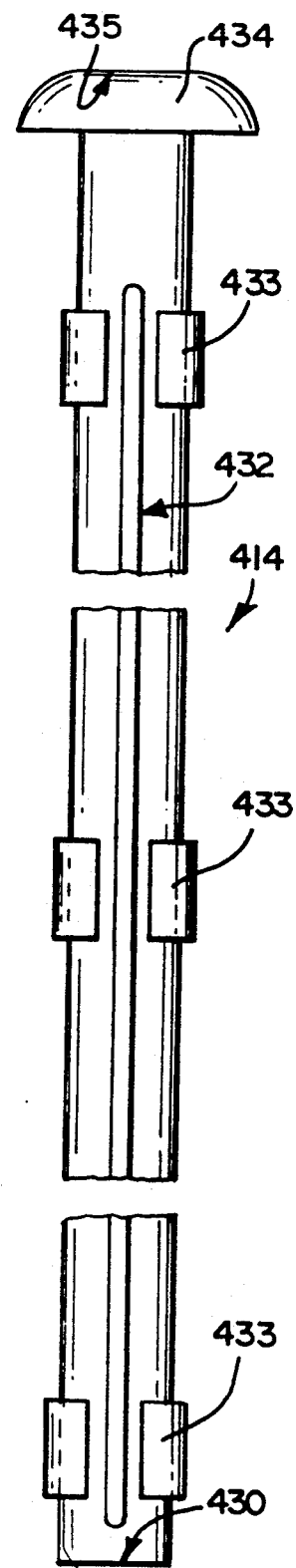
FIG. 10 corresponds to FIG. 3 and shows a reinforced outer sleeve.

With reference to FIG. 10, to reinforce the sleeve 414 to make it more rigid, bearing in mind the weakening effect of the slot 432, a plurality of discontinuous reinforcing bands 433 is provided externally around the sleeve, but still leaving the slot 432 clear.

Advantages of the invention are that representative samples to a higher degree than what was possible with prior art devices can be sampled, that sampling devices in accordance with the invention are simple and inexpensive to manufacture and that operation of the sampling device in accordance with the invention is simple and can be effected by means of samplers who are capable of using known prior art devices.

I claim:

1. A method of sampling grain offered in bulk, including inserting an empty, elongate container, which has a hollow interior in the form of a passage extending from a first end which will be a lower end in use to an opposed second end which is open and which will be an upper end in use, and elongate inlet means along its length and in communication with the passage, substantially vertically into the bulk of grain while covering the elongate inlet means;

uncovering in an axial direction the inlet means and exposing the interior of the container progressively from the bottom of the bulk upwardly to allow grain, correspondingly progressively, to flow into the container from a position toward the bottom of the bulk to a position upwardly spaced from the bottom of the bulk;

re-covering the inlet means;

withdrawing the container; and upturning the container into a repository to empty it via said passage and said open second end.

2. A method as claimed in claim 1 which includes agitating the grain where the inlet means is being uncovered.

3. A method as claimed in claim 1 in which uncovering and re-covering the elongate inlet means is by appropriately sliding a sleeve, which surrounds the container, longitudinally relative to the container respectively to uncover and to re-cover the elongate inlet means.

4. A sampling device suitable for use in sampling grain offered in bulk, the device comprising a container of elongate shape having a closed lower end, an opposed upper end which is open, and a hollow interior in the form of a passage extending from the closed lower end to the open upper end, the container being adapted for insertion into a bulk of grain;

inlet means into the hollow interior, the inlet means extending from about the closed lower end along the container toward the open upper end;

axially movable closing means for selectively covering the inlet means and operable for progressively uncovering the inlet means commencing from said closed lower end, the sampling device being suitable, when a sample has been collected in use, to be upturned to be emptied via said passage and said open upper end of the container.

5. A sampling device as claimed in claim 4 in which the inlet means includes a composite opening formed of a plurality of ports arranged in series in longitudinal alignment.

6. A sampling device as claimed in claim 4 in which the container is in the form of a round cylindrical tube and in which the axially movable closing means includes an open ended sleeve fitting snugly, such as to allow axial sliding, over the tube.

7. A sampling device suitable for use in sampling grain offered in bulk, the device comprising a container of elongate shape in the form of a round cylindrical tube having a closed lower end adapted for insertion into a bulk of grain;

inlet means including a composite opening formed of a plurality of ports arranged in longitudinal alignment in series and extending from about the closed lower end along the container;

closing means including an open ended sleeve fitting snugly, such as to allow axial sliding, over the tube for selectively covering the inlet means and operable for progressively uncovering the inlet means commencing from said lower end, in which the tube has a laterally extending handle toward an upper end thereof, the sleeve having a corresponding slot to allow passage of the handle during axial sliding of the sleeve relative to the container in use.

8. A sampling device as claimed in claim 7 in which the sleeve has a handle at or toward an upper end thereof.

9. A sampling device, adapted to sample grain from a reservoir of a depth more than about 1,5 m, which device comprises
- a container of elongate shape in the form of a round cylindrical tube having a closed lower end adapted for insertion into a bulk of grain;
- inlet means including a composite opening formed of a plurality of ports arranged in longitudinal alignment in series and extending from about the closed lower end along the container;
- closing means including an open ended sleeve fitting snugly, such as to allow axial sliding, over the tube for selectively covering the inlet means and operable for progressively uncovering the inlet means commencing from said lower end, in which device
- said inlet means is in the form of lower inlet means extending from about the closed lower end along a lower portion of the container; and
- the closing means is in the form of lower closing means for selectively covering the lower inlet means and operable for progressively uncovering the lower inlet means commencing from said lower end;
- the device including
- higher inlet means extending from a position beyond the lower inlet means along a higher portion of the container; and
- higher closing means for selectively covering the higher inlet means and operable for substantially simultaneously uncovering the higher inlet means after the lower inlet means has been uncovered.

10. A grain sampling device as claimed in claim 9 in which the higher inlet means is substantially an extension of the lower inlet means.

11. A grain sampling device as claimed in claim 10 in which the higher closing means includes exposing means in the form of a series of ports along a predetermined portion of the length of the sleeve, said ports being angularly offset from the higher inlet means, and the sleeve being adapted to be twisted in use to register the ports with the higher inlet means.

12. A method of sampling grain offered in bulk in a grain reservoir of a depth more than about 1,5 m, including
- inserting an empty, elongate container substantially vertically into the bulk of grain while covering elongate inlet means of the container;
- uncovering in an axial direction the inlet means and, in respect of a lower portion of the bulk of grain, exposing the interior of the container progressively from the bottom of the bulk upwardly to allow grain, correspondingly progressively, to flow into the container from a position toward the bottom of the bulk to a position toward the top of said lower portion of the bulk of the grain; and
- subsequently, exposing the interior of the container to a higher portion of the bulk of grain substantially simultaneously and allowing the grain from said higher portion to flow into the container.

13. A method as claimed in claim 12 in which exposing the interior of the container to said higher portion of the bulk of grain includes bringing an opening in the container and an opening in a sleeve surrounding the container at a depth corresponding to the position of said higher portion of the bulk of grain, into register.

* * * * *